United States Patent
Miyazaki et al.

(10) Patent No.: US 12,265,083 B2
(45) Date of Patent: *Apr. 1, 2025

(54) IMMUNOASSAY METHOD FOR FREE AIM IN BIOLOGICAL SAMPLE, AND ASSAY KIT

(71) Applicants: SEKISUI MEDICAL CO., LTD., Tokyo (JP); Toru Miyazaki, Tokyo (JP); SOCIAL WELFARE ORGANIZATION "SAISEIKAI" IMPERIAL GIFT FOUNDATION INC., Tokyo (JP)

(72) Inventors: Toru Miyazaki, Tokyo (JP); Takeshi Okanoue, Suita (JP); Tomohide Asai, Tokyo (JP); Yuka Kanetsuki, Tokyo (JP); Jiro Hirota, Tokyo (JP)

(73) Assignees: SEKISUI MEDICAL CO., LTD., Tokyo (JP); Miyazaki Toru, Tokyo (JP); SOCIAL WELFARE ORGANIZATION "SAISEIKAI" IMPERIAL GIFT FOUNDATION INC., Tokyo (JP)

( * ) Notice: Subject to any disclaimer, the term of this patent is extended or adjusted under 35 U.S.C. 154(b) by 855 days.

This patent is subject to a terminal disclaimer.

(21) Appl. No.: 17/427,559

(22) PCT Filed: Jan. 30, 2020

(86) PCT No.: PCT/JP2020/003415
§ 371 (c)(1),
(2) Date: Jul. 30, 2021

(87) PCT Pub. No.: WO2020/158857
PCT Pub. Date: Aug. 6, 2020

(65) Prior Publication Data
US 2022/0107318 A1 Apr. 7, 2022

(30) Foreign Application Priority Data
Jan. 31, 2019 (JP) .................................. 2019-015220

(51) Int. Cl.
*G01N 33/53* (2006.01)
*G01N 33/577* (2006.01)

(52) U.S. Cl.
CPC ........... *G01N 33/577* (2013.01); *G01N 33/53* (2013.01); *G01N 33/5306* (2013.01)

(58) Field of Classification Search
CPC ... G01N 33/577; G01N 33/5306; G01N 33/00
See application file for complete search history.

(56) References Cited

U.S. PATENT DOCUMENTS

| | | |
|---|---|---|
| 2015/0094268 A1 | 4/2015 | Miyazaki |
| 2018/0224437 A1 | 8/2018 | Miyazaki |
| 2019/0317096 A1 | 10/2019 | Miyazaki et al. |

FOREIGN PATENT DOCUMENTS

| | | |
|---|---|---|
| EP | 2 870 970 A1 | 5/2015 |
| EP | 3 919 906 A1 | 12/2021 |
| WO | WO 2013/162021 A1 | 10/2013 |
| WO | WO 2017/022315 A1 | 2/2017 |
| WO | WO 2017/043617 A1 | 3/2017 |

OTHER PUBLICATIONS

Arai et al., Nat. Med., 2016, vol. 22(2):183-193.*
"CircuLex Human AIM/CD5L/Spα ELISA Kit" User's Manual, MBL, 2014, [online], [retrieved on Mar. 3, 2020], Retrieved from the Internet: <URL:https://www.mblintl.com/assets/CY-8080-v141003.pdf>, Cat# CY-8080, Version#: 141003, pp. 1-17.
Arai et al., "Apoptosis inhibitor of macrophage protein enhances intraluminal debris clearance and ameliorates acute kidney injury in mice", Nature Medicine, Articles, vol. 22, No. 2, Feb. 2016, pp. 183-193.
Arai et al., "Obesity-Associated Autoantibody Production Requires AIM to Retain the Immunoglobulin M Immune Complex on Follicular Dendritic Cells", Cell Reports, Apr. 25, 2013, vol. 3, No. 4, pp. 1187-1198.
International Search Report for PCT/JP2020/003415 (PCT/ISA/210) mailed on Mar. 31, 2020.
Miyazaki et al., "AIM associated with the IgM pentamer: attackers on stand-by at aircraft carrier", Cellular & Molecular Immunology, Jan. 29, 2018, vol. 15, pp. 563-574.
Written Opinion of the International Searching Authority for PCT/JP2020/003415 (PCT/ISA/237) mailed on Mar. 31, 2020.
Extended European Search Report for European Application No. 20747776.1, dated Oct. 5, 2022.
International Preliminary Report on Patentability and English translation of the Written Opinion of the International Searching Authority for International Application No. PCT/JP2020/003415, dated Aug. 12, 2021.
European Office Action for European Application No. 20 747 776.1, dated Jun. 22, 2023.
Chinese Office Action and Search Report for Chinese Application No. 202080011490.9, dated Mar. 9, 2024, with English translation.

* cited by examiner

*Primary Examiner* — Xiaozhen Xie

(74) *Attorney, Agent, or Firm* — Birch, Stewart, Kolasch & Birch, LLP

(57) ABSTRACT

A problem to be solved is to improve the specificity of an anti-AIM antibody for free AIM in a biological sample containing complex AIM and free AIM.

The problem can be solved by an immunoassay method for measuring an amount of free AIM in a biological sample containing complex AIM and free AIM, and the method comprises bringing the biological sample into contact with an anti-AIM antibody in the presence of an anti-IgM antibody.

7 Claims, 1 Drawing Sheet

Specification includes a Sequence Listing.

| ADDED ANTI-IgM ANTIBODY | SAMPLE | COUNT (-blank) | COUNT RATIO (STANDARD: NORMAL) | COUNT INCREASE/DECREASE RATIO |
|---|---|---|---|---|
| STANDARD (WITHOUT ANTI-IgM ANTIBODY) | F6+F7 | 25820.7 | 100% | 0% |
| | F14+F15 | 12871.3 | 100% | 0% |
| HBR-6 | F6+F7 | 9648.0 | 37.4% | -62.6% |
| | F14+F15 | 12899.0 | 100.2% | 0.2% |
| HBR-20 | F6+F7 | 14399.4 | 55.8% | -44.2% |
| | F14+F15 | 10814.6 | 84.0% | -16.0% |
| P0911 | F6+F7 | 1139.2 | 4.4% | -95.6% |
| | F14+F15 | 9054.7 | 70.3% | -29.7% |

IMMUNOASSAY METHOD FOR FREE AIM IN BIOLOGICAL SAMPLE, AND ASSAY KIT

TECHNICAL FIELD

The present invention relates to an immunoassay method for free AIM in a biological sample. The present invention also relates to an assay kit for measuring an amount of free AIM in a biological sample. The present invention also relates to a method for suppressing a non-specific reaction in an immunoassay method for measuring an amount of free AIM in a biological sample.

BACKGROUND ART

AIM (apoptosis inhibitor of macrophage) is a secretory blood protein with a molecular weight of about 50 kDa produced by tissue macrophages. AIM has a structure in which three scavenger recipient cysteine-rich (SRCR) domains having specific sequences containing many cysteine residues are connected in tandem, and the cysteine residues are considered to be disulfide-bonded to each other in each domain to form a compact spherical three-dimensional structure.

AIM is known to have the characteristic of binding to various molecules such as lipopolysaccharide, IgM, complement regulatory factors, and fatty acid synthetases. Particularly, AIM is known to exist in the form of a complex with IgM in the blood. Since IgM is a huge protein complex exceeding 500 kDa, AIM does not pass through the glomerulus and transfer to urine as long as AIM is bound to IgM, and a high blood concentration of AIM is maintained. When dissociated from IgM, AIM is promptly excreted into urine. Therefore, most of AIM forms a complex with IgM in the blood and are rarely present in the blood in a free state rather than as a conjugate.

In recent years, it has been clarified that AIM is involved in the progression of pathological conditions in various diseases such as insulin resistance or arteriosclerosis. For example, a relationship between free AIM present in a free form not bound to another binding partner and liver disease has been reported (Patent Document 1).

CITATION LIST

Patent Literature

Patent Document 1: WO 2017/043617

SUMMARY OF INVENTION

Technical Problem

When a specific disease is diagnosed based on a measurement result of a free AIM amount, it is necessary to eliminate an amount of AIM forming a complex and measure only the free AIM amount. However, when free AIM is detected, complex AIM bound to another binding partner may also be detected. Therefore, a demand exists for a technique capable of eliminating a non-specific reaction of AIM forming a complex without complicated operations.

An object of the present invention is to provide an immunoassay method for measuring an amount of free AIM in a biological sample containing complex AIM and free AIM with excellent specificity, and an assay kit for measuring an amount of free AIM in a biological sample containing complex AIM and free AIM with excellent specificity.

Solution to Problem

An antibody binding to both free AIM and complex AIM is more easily obtained than an antibody specifically binding only to free AIM. As a result of intensive studies for solving the problem by using the easily-obtained antibody binding to both free AIM and complex AIM, the present inventors found that the specificity of an anti-AIM antibody for free AIM can be improved by bringing a biological sample into contact with the anti-AIM antibody in the presence of an anti-IgM antibody, thereby completing the present invention.

Specifically, the present invention is as follows.

<1> An immunoassay method for measuring an amount of free AIM in a biological sample containing complex AIM and free AIM, the method comprising: bringing the biological sample into contact with an anti-AIM antibody in a presence of an anti-IgM antibody.

<2> The immunoassay method for measuring an amount of free AIM in a biological sample according to <1>, wherein the biological sample is a body fluid sample.

<3> The immunoassay method for measuring an amount of free AIM in a biological sample according to <1> or <2>, wherein the biological sample is blood, serum, plasma, or urine.

<4> The immunoassay method for measuring an amount of free AIM in a biological sample according to any one of <1> to <3>, wherein the anti-AIM antibody is a polyclonal antibody.

<5> An assay kit for measuring an amount of free AIM in a biological sample containing complex AIM and free AIM, comprising: an anti-IgM antibody; and an anti-AIM antibody.

<6> The assay kit for measuring an amount of free AIM in a biological sample according to <5>, wherein the biological sample is a body fluid sample.

<7> The assay kit for measuring an amount of free AIM in a biological sample according to <5> or <6>, wherein the biological sample is blood, serum, plasma, or urine.

<8> The assay kit for measuring an amount of free AIM in a biological sample according to any one of <5> to <7>, wherein the anti-AIM antibody is a polyclonal antibody.

<9> A method for suppressing a non-specific reaction in an immunoassay method for measuring an amount of free AIM in a biological sample containing complex AIM and free AIM, the method comprising: bringing the biological sample into contact with an anti-AIM antibody in a presence of an anti-IgM antibody.

<10> The method for suppressing a non-specific reaction according to <9>, wherein the biological sample is a body fluid sample.

<11> The method for suppressing a non-specific reaction according to <9> or <10>, wherein the non-specific reaction is a non-specific reaction due to IgM in the biological sample.

Advantageous Effects of Invention

According to the present invention, the specificity of an anti-AIM antibody for free AIM can be improved in an immunoassay method for measuring an amount of free AIM in a biological sample containing complex AIM and free AIM.

BRIEF DESCRIPTION OF DRAWINGS

FIG. 1 is a diagram showing a non-specific reaction suppressing effect when various anti-human IgM antibodies are added to a measurement system.

DESCRIPTION OF EMBODIMENTS

[1] Immunoassay Method for Measuring Amount of Free AIM in Biological Sample (Biological Sample)

Examples of a biological sample analyzable in the present invention include solid tissues and body fluids derived from living bodies (organisms), and body fluids are preferably used. The biological sample analyzable in the present invention is more preferably a body fluid sample such as blood, serum, plasma, urine, saliva, sputum, tear fluid, otorrhea, or prostatic fluid, further preferably blood, serum, plasma, or urine. Examples of the living body or the subject include humans or animals (e.g., mice, guinea pigs, rats, monkeys, dogs, cats, hamsters, horses, bovines, and pigs), and are preferably humans. The biological sample from the subject may be collected or prepared at the time of implementation of the present invention or may preliminarily be collected or prepared and stored. The person measuring the sample and the person measuring an amount of free AIM in the sample may be different. The biological sample can be an in vivo sample. In the present invention, the biological sample contains both free AIM and complex AIM.

(AIM)

AIM (apoptosis inhibitor of macrophage) is a secretory blood protein with a molecular weight of about 50 kDa produced by tissue macrophages. AIM has a structure in which three scavenger recipient cysteine-rich (SRCR) domains, i.e., specific sequences containing many cysteine residues, are connected in tandem, and the cysteine residues are considered to be disulfide-bonded to each other in each domain to form a compact spherical three-dimensional structure.

Human AIM is composed of 347 amino acids represented by SEQ ID NO: 1 and contains three SRCR domains rich in cysteine. The SRCR1 domain corresponds to amino acid numbers 24 to 125 in the amino acid sequence represented by SEQ ID NO: 1. The SRCR2 domain corresponds to amino acid numbers 138 to 239 in the amino acid sequence represented by SEQ ID NO: 1. The SRCR3 domain corresponds to amino acid numbers 244 to 346 in the amino acid sequence represented by SEQ ID NO: 1.

The amino acid sequence of human AIM is as follows.

```
                                    (SEQ ID NO: 1)
MALLFSLILAICTRPGFLASPSGVRLVGGLHRCEG

RVEVEQKGQWGTVCDDGWDIKDVAVLCRELGCAA

SGTPSGILYEPPAEKEQKVLIQSVSCTGTEDTLAQ

CEQEEVYDCSHDEDAGASCENPESSFSPVPEGVRL

ADGPGHCKGRVEVKHQNQWYTVCQTGWSLRAAKVV

CRQLGCGRAVLTQKRCNKHAYGRKPIWLSQMSCSG

REATLQDCPSGPWGKNTCNHDEDTWVECEDPFDLR

LVGGDNLCSGRLEVLHKGVWGSVCDDNVVGEKEDQ

VVCKQLGCGKSLSPSFRDRKCYGPGVGRIWLDNVR

CSGEEQSLEQCQHRFWGFHDCTHQEDVAVICSG
```

Specifically, the amino acid sequences of the SRCR1 domain, the SRCR2 domain, and the SRCR3 domain in human AIM are as follows.

```
SRCR1 domain:
                                    (SEQ ID NO: 2)
VRLVGGLHRCEGRVEVEQKGQWGTVCDDGWDIKDV

AVLCRELGCGAASGTPSGILYEPPAEKEQKVLIQS

VSCTGTEDTLAQCEQEEVYDCSHDEDAGASCE

SRCR2 domain:
                                    (SEQ ID NO: 3)
VRLADGPGHCKGRVEVKHQNQWYTVCQTGWSLRAA

KVVCRQLGCGRAVLTQKRCNKHAYGRKPIWLSQMS

CSGREATLQDCPSGPWGKNTCNHDEDTWVECE

SRCR3 domain:
                                    (SEQ ID NO: 4)
LRLVGGDNLCSGRLEVLHKGVWGSVCDDNVVGEKE

DQVVCKQLGCGKSLSPSFRDRKCYGPGVGRIWLDN

VRCSGEEQSLEQCQHRFWGFHDCTHQEDVAVICS
```

(Free AIM)

In this description, the "free AIM" means AIM existing in a free state without being bound to other substances such as lipopolysaccharide or IgM. On the other hand, in this description, AIM bound to other substances such as lipopolysaccharide or IgM and existing in a state of a complex is referred to as complex AIM. The free AIM is preferably human free AIM, and the complex AIM is preferably human complex AIM.

(Anti-IgM Antibody)

The term "anti-IgM antibody" as used herein means an antibody having a property of binding to IgM. In other words, the "anti-IgM antibody" means a substance from which human IgM and a precipitation line are generated by the Ouchterlony method. The antibody may have a binding property to another antigen as long as the antibody has a binding property to IgM and the effect of the present invention is not impaired. The anti-IgM antibody used in the present invention is preferably an anti-human IgM antibody. As the anti-IgM antibody used in the present invention, both a polyclonal antibody and a monoclonal antibody can be used. The anti-IgM antibody may be a functional fragment capable of binding to IgM.

In the immunoassay method of the present invention, by using the anti-IgM antibody, the non-specific reaction due to complex AIM can be reduced to 50% or less, preferably 60% or less, further preferably 70% or less, most preferably 90% or less, as compared to the case where the anti-IgM antibody is not added.

Although the reason why the effect is obtained in the present invention is not sufficiently clarified yet, the binding between the IgM portion of the complex AIM and the anti-IgM antibody probably inhibits the binding between the AIM portion of the complex AIM and the anti-AIM antibody. It is surprising that the binding of the antibody to one of the binding partners affects the binding of the antibody to the other of the binding partners.

A commercially available anti-IgM antibody can also be used as the anti-IgM antibody used in the present invention. The commercially available anti-IgM antibody can be HBR-1, HBR-3, HBR-6, HBR-Plus, HBR-9, HBR-11, HBR20, HBR21, HBR22, HBR23, HBR24, HBR25, HBR26 (SCANTIBODIES), P0911 (Trina Bioreactives AG), and TRU Block (registered trademark) ULTRA (Meridian Bioscience), preferably HBR-6, HBR-20, and/or a commercially available anti-human IgM polyclonal antibody, more preferably HBR-6, HBR-20, and/or P0911 (Trina Bioreactives AG).

The additive concentration of the anti-IgM antibody is not particularly limited as long as a sufficient non-specific reaction suppressing effect is achieved and a main reaction of immunological measurement is not affected, and in the case of a monoclonal antibody, the antibody is desirably used in a concentration range of 1 to 1000 μg/mL, more desirably 10 to 1000 μg/mL, further desirably 10 to 300 μg/mL. In the case of a polyclonal antibody, the antibody is desirably used in a concentration range of 0.01 to 2 wt %, desirably used in a concentration range of 0.03 to 2 wt %, further desirably used in a concentration range of 0.05 to 1 wt %.

In the present invention, the binding affinity of the anti-IgM antibody to IgM is not particularly limited as long as the effect of the present invention can be obtained, and, for example, the binding affinity to IgM can be Kd of at least about $10^{-4}$ M, at least about $10^{-5}$ M, at least about $10^{-6}$ M, at least about $10^{-7}$ M, at least about $10^{-8}$ M, at least about $10^{-9}$ M, at least about $10^{-10}$ M, at least about $10^{-11}$ M, at least about $10^{-12}$ M or more.

The anti-IgM antibody can be prepared as either a monoclonal antibody or a polyclonal antibody according to a known method. The monoclonal antibody can be obtained by, for example, isolating spleen cells or lymph node cells, which are antibody-producing cells, from a non-human mammal immunized with IgM or IgM fragments, by fusing the cells with a myeloma-derived cell line having a high proliferative capacity to produce a hybridoma, and purifying an antibody produced by this hybridoma. The polyclonal antibody can be obtained from the serum of an animal immunized with IgM or IgM fragments. Examples of immunogens include, but not limited to, IgM or IgM fragments of primates such as humans and monkeys, rodents such as rats and mice, dogs, cats, horses, sheep, and pigs.

The anti-IgM antibody can be a whole antibody molecule as well as a fragment of an antibody having an antigen-antibody reaction activity and can be an antibody obtained through an immunization step of an animal as described above or obtained by using a gene recombination technique or can be a chimeric antibody. The fragment of the antibody is preferably a functional fragment; examples thereof include F(ab')2, Fab', scFv, etc.; and these fragments can be produced by processing the antibody obtained as described above with a proteolytic enzyme (e.g., pepsin or papain), or by cloning of DNA of the antibody and expression in a culture system using *Escherichia coli* or yeast.

In this description, "non-specific reaction" means that a substance other than free AIM binds to the anti-AIM antibody used in the present invention. In the present invention, a non-specific reaction due to complex AIM, or particularly, complex AIM having IgM bound as a binding partner can be suppressed by using the anti-IgM antibody. In other words, in the present invention, the specificity of the anti-AIM antibody for free AIM can be improved by using the anti-IgM antibody.

A method for suppressing a non-specific reaction in immunological analysis of an amount of free AIM in a biological sample containing complex AIM and free AIM of the present invention can be a method for inhibiting binding of complex AIM and an anti-AIM antibody in immunological analysis of an amount of free AIM, including bringing a biological sample containing complex AIM and free AIM with an anti-AIM antibody in the presence of an anti-IgM antibody.

(Anti-AIM Antibody)

In this description, an antibody reacting with both complex AIM and free AIM in the absence of an anti-IgM antibody is referred to as an anti-AIM antibody. The term "anti-AIM antibody" as used herein does not include an antibody specific for free AIM reacting with free AIM and substantially not reacting with complex AIM. In this description, "reacting with free AIM and not substantially reacting with complex AIM" means that when a reactivity of an antibody is measured by a method known to those skilled in the art, the binding force to complex AIM is less than 10% when the binding force to free AIM is 100.

Although the "anti-AIM antibody" of the present invention may be any of the anti-AIM antibody having the reactivity to complex AIM and the reactivity to free AIM at the same level, the anti-AIM antibody having the reactivity to free AIM stronger than the reactivity to complex AIM, and the anti-AIM antibody having the reactivity to complex AIM stronger than the reactivity to free AIM when the reactivity of the antibody is measured by a method known to those skilled in the art, the anti-AIM antibody having the reactivity to free AIM stronger than the reactivity to complex AIM is preferably used. More specifically, when the reactivity of the antibody is measured by a method known to those skilled in the art, it is preferable to use the anti-AIM antibody having the reactivity to complex AIM of 50% or less when the binding force to free AIM is 100.

The anti-AIM antibody used in the immunoassay method of the present invention can be an antibody binding to an epitope in the SRCR3 domain of human AIM. The anti-AIM antibody used in the immunoassay method of the present invention preferably binds to an epitope in the SRCR3 domain and does not bind to the SRCR1 domain. The anti-AIM antibody used in the immunoassay method of the present invention more preferably binds to an epitope in the SRCR3 domain and does not bind to either the SRCR1 domain or the SRCR2 domain.

The anti-AIM antibody used in the present invention reacts with both complex AIM and free AIM in the absence of anti-IgM antibody. The presence of the anti-IgM antibody in the reaction system can reduce the reactivity with the complex AIM. Although the timing of adding the anti-IgM antibody to the measurement system is not particularly limited as long as the effects of the present invention can be obtained, the anti-IgM antibody is preferably added before or at the same time as the addition of the anti-AIM antibody.

The anti-AIM antibody can be prepared as either a monoclonal antibody or a polyclonal antibody according to a known method. The monoclonal antibody can be obtained by, for example, isolating spleen cells or lymph node cells, which are antibody-producing cells, from a non-human mammal immunized with free AIM or a free AIM fragment and/or complex AIM or a complex AIM fragment, fusing the cells with a myeloma-derived cell line having a high proliferative capacity to produce a hybridoma, and purifying an antibody produced by this hybridoma. The polyclonal antibody can be obtained from the serum of an animal immunized with free AIM or a free AIM fragment and/or complex AIM or a complex AIM fragment. Examples of immunogens include, but not limited to, free AIM or free AIM fragments and/or complex AIM or complex AIM fragments of primates such as humans and monkeys, rodents such as rats and mice, dogs, cats, horses, sheep, and pigs. For example, the anti- AIM monoclonal antibody can be produced by the following procedure as in examples of Patent Document 1.

<Animal Sensitization>

Emulsion is produced by mixing full-length human rAIM (2 mg/ml) as an antigen with an equal amount of TiterMax Gold (G-1 Funakoshi). Two 8-week-old female Balb/c mice (Charles River Laboratories) are used as immunized animals, and 50 µL of an antigen solution is administered to the sole of the hind foot. The same administration is performed 2 weeks later, and after another 2 weeks or more, 50 µg of the antigen solution is administered to the sole of the hind foot to prepare for cell fusion performed 3 days later.

<Myeroma Cells>

Mouse P3U1 is used for myeloma cells, and a medium used for growth culture is obtained by adding glutamine and pyruvic acid to RPMI1640 (11875-119 GIBCO) and adding FBS (S1560 BWT) at 10%. Penicillin and streptomycin are added as antibiotics in appropriate amounts.

<Cell Fusion>

Popliteal lymph nodes are aseptically removed from the mice after cardiac blood is collected under anesthesia and are placed on a beaker with #200 mesh and pressed with a silicon rod to prepare a cell suspension. The cells are centrifugally washed twice in RPMI 1640 and then the number of cells is counted. Myeloma cells in the logarithmic growth phase are collected by centrifugation, washed, and then adjusted so that the ratio of lymphocytes to myeloma cells is 5:1, and mixing centrifugation is performed. Cell fusion is performed by using PEG1500 (783641 Roche). Specifically, after a cell pellet is reacted with 1 mL of PEG solution for 3 minutes, then diluted in stages, and washed by centrifugation, a medium is added, and 200 µL is placed in each of 15 96-well plates for 1 week of culture. For the medium, a HAT supplement (21060-017 GIBCO) is added to a medium for myeloma cells to adjust the FBS concentration to 15%.

<Mouse Ascites Collection>

After the cryopreserved cells are thawed and proliferation culture is performed, $1 \times 10^7$ cells were administered to the abdominal cavity of a nude mouse (BALB/cAJcl-nu/nu Nippon Clea) to which 0.5 ml of pristane (42-002 Cosmo Bio) was intraperitoneally administered 1 week or more before, and after about 2 weeks, 4 to 12 ml of ascites is obtained. After removing a solid matter by centrifugation, the ascites was cryopreserved.

The anti-AIM antibody can be a whole antibody molecule as well as a fragment of an antibody having an antigen-antibody reaction activity. The anti-AIM antibody can be an antibody obtained through an immunization step of an animal as described above or obtained by using a gene recombination technique or can be a chimeric antibody. The fragment of the antibody is preferably a functional fragment, and examples thereof include $F(ab)_2$, Fab', scFv, etc. These fragments can be produced by processing the antibody obtained as described above with a proteolytic enzyme (e.g., pepsin or papain), or by cloning of DNA of the antibody and expression in a culture system using *Escherichia coli* or yeast.

Although "reacting" with AIM, "recognizing" AIM, and "binding" to AIM are synonymously used in this description, these must be construed in the broadest sense without being limited to these exemplifications. Whether an antibody "reacts" with an antigen (compound) such as AIM can be confirmed by an antigen solid phase ELISA method, a competitive ELISA method, a sandwich ELISA method, etc. as well as by a method (SPR method) using the principle of surface plasmon resonance etc. The SPR method can be performed by using devices, sensors, and reagents commercially available under the name of Biacore (registered trademark).

In this description, an "insoluble carrier" may be represented as a "solid phase", and physically or chemically supporting an antigen or antibody with an insoluble carrier or the supporting state may be represented as "immobilizing", "immobilized", or "solid phased". The term "analysis", "detection", or "measurement" must be construed in the broadest sense, including the existence proof and/or the quantitation of free AIM and must not be construed in a limited manner in any sense.

(Immunoassay Method)

Examples of the immunoassay method of the present invention include, but not limited to, electrochemiluminescence immunoassay (ECL method), ELISA, enzyme immunoassay, an immunohistochemical staining method, a surface plasmon resonance method, latex agglutination immunoassay, chemiluminescence immunoassay, a fluorescent antibody method, radioimmunoassay, an immunoprecipitation method, a Western Blot method, immunochromatography, the EATA method (Electrokinetic Analyte Transport Assay), and high performance liquid chromatography (HPLC), which are techniques known to those skilled in the art.

By using a labeled antibody (secondary antibody) that can bind to the antibody used, an amount of the antibody bound to free AIM can be measured, and an amount of free AIM in a biological sample can thereby be measured. Examples of a labeling substance for producing the labeled antibody include enzymes, fluorescent substances, chemical luminescent substances, biotin, avidin, radioisotopes, colloidal gold particles, or colored latex. Those skilled in the art can appropriately select an immunoassay method depending on an antibody and a labeling substance used and, since an experimental system can easily be constructed, the electrochemiluminescence immunoassay (ECL method) is preferably used.

The electrochemiluminescence immunoassay (ECL method) means a method for calculating an amount of an analyte by causing a labeling substance to emit light by an electrochemical stimulus and detecting an amount of luminescence. In the electrochemiluminescence immunoassay (ECL method), a ruthenium complex can be used as a labeling substance. The amount of luminescence of this ruthenium complex can be detected by disposing an electrode on a solid phase (microplate or beads etc.) and causing an electrochemical stimulus on the electrode.

The electrochemiluminescence immunoassay (ECL method) can be performed by using an anti-AIM antibody as a solid phase antibody and another anti-AIM antibody (i.e., an antibody recognizing an epitope different from the solid phase antibody) as a detection antibody (labeled antibody) in the presence of an anti-IgM antibody. When the solid phase antibody and the labeled antibody are used while beads and a ruthenium complex are used as a solid phase and a label, respectively, the measurement principle is as follows. The following describes the measurement principle in an embodiment of the present invention and does not limit the scope of the present invention at all.

1. When the beads having the anti-AIM antibody bound thereto are reacted with a sample in the presence of the anti-IgM antibody, the free AIM in the sample binds to the antibody bound to the beads.

2. After washing the beads, a ruthenium-labeled antibody (an antibody having a recognition epitope different from the antibody bound to the beads) is reacted with the free AIM bound to the beads and is bound in a sandwich shape.

3. After washing the beads, when electrical energy is applied on the electrode, the ruthenium complex emits light depending on an amount of the ruthenium-labeled antibody bound to the beads via the free AIM. By measuring this amount of luminescence, the free AIM in the sample can be measured.

Among the methods for immunological analysis, the ELISA method using an enzyme label is also preferable since a target can easily and quickly be measured. In the case of sandwich ELISA, an insoluble carrier having an anti-AIM antibody immobilized thereon and an anti-AIM antibody labeled with a labeling substance and having an epitope different from the immobilized antibody can be used. In this case, the insoluble carrier is preferably a plate (immunoplate), and the labeling substance can appropriately be selected and used.

The antibody immobilized on the insoluble carrier captures the free AIM in the sample in the presence of the anti-IgM antibody and forms an antibody-free AIM complex on the insoluble carrier. The antibody labeled with the labeling substance binds to the captured free AIM to form a sandwich with the antibody-free AIM complex described above. The free AIM in the sample can be measured by measuring an amount of the labeling substance by a method corresponding to the labeling substance. For specific methods, such as a method for immobilizing the antibody on the insoluble carrier and a method for binding the antibody and the labeling substance, the methods well known to those skilled in the art can be used without limitation.

The high performance liquid chromatography method (HPLC method) can also be used. In this case, a fluorescently-labeled anti-AIM antibody is brought into contact with a biological sample so that the anti-AIM antibody is bound to the free AIM and the complex AIM. Subsequently, only the anti-AIM antibody bound to the free AIM can be separated by HPLC.

A latex immunoagglutination method (hereinafter also referred to as an LTIA method) is a typical particle agglutination immunoassay and is also preferable as the immunoassay method. In the LTIA method, latex particles carrying an antibody to a target component are used, and a degree of agglutination (turbidity) of the latex particles caused by binding between an antigen that is the target component and the antibody-supporting latex particles forming an antigen-antibody complex is detected by optical means (e.g., a turbidimetric method for measuring transmitted light, a turbidity method for measuring scattered light), so that the target component can be analyzed. In the immunoassay method of the present invention, latex particles carrying the anti-AIM antibody are used, and a degree of agglutination of the latex particles caused by binding between free AIM that is the target component and the antibody-supporting latex particles forming an antigen-antibody complex in the presence of the anti-IgM antibody can be detected by optical means.

The high performance liquid chromatography method (HPLC method) or the EATA method (Electrokinetic Analyte Transport Assay) can also be used as the immunoassay method. The EATA method can be performed by using μTAS Wako i30 manufactured by FUJIFILM Wako Pure Chemical Corporation.

[2] Assay Kit for Measuring Amount of Free AIM

An assay kit for measuring an amount of free AIM of the present invention includes an anti-IgM antibody and an anti-AIM antibody. The assay kit of the present invention can also include other test reagents, specimen diluents, and/or instructions for use.

The assay kit for measuring an amount of free AIM of the present invention preferably includes (1) to (3) below:

(1) a solid phase on which a first anti-AIM monoclonal antibody is immobilized;

(2) a second anti-AIM antibody labeled with an electrochemical luminescent substance and having an epitope different from the first anti-AIM antibody; and (3) an anti-IgM antibody.

When using the ECL method, the assay kit of the present invention can include a solid phase on which the first anti-AIM antibody is immobilized and a second anti-AIM antibody labeled with an electrochemical luminescent substance such as a ruthenium complex. For example, in the assay kit using microbeads as the solid phase, a biological sample is added to and reacted with the microbeads on which the first anti-AIM antibody is immobilized in the presence of an anti-IgM antibody, the sample is then removed and washed. Subsequently, the second anti-AIM antibody labeled with an electrochemical luminescent substance and recognizing an epitope different from the first anti-AIM antibody is added and reacted. After washing the microbeads, electric energy is applied for luminescence, and an amount of luminescence of the labeling substance can be measured to obtain a free AIM concentration.

When the sandwich ELISA method is used, the assay kit includes at least (1) to (3) below:

(1) an insoluble carrier on which a first anti-AIM antibody (solid phase antibody) is immobilized;

(2) a second anti-AIM antibody (labeled antibody) labeled with a labeling substance and recognizing an epitope different from the first anti-AIM antibody; and (3) an anti-IgM antibody.

In such an assay kit, first, a biological sample is added to the insoluble carrier on which the first anti-AIM antibody is immobilized in the presence of the anti-IgM antibody, and is then incubated, and the sample is removed and washed. The labeled antibody is added and then incubated, and a substrate is added for coloring. The free AIM concentration in the biological sample can be obtained by measuring the coloring with a plate reader etc.

When the LTIA method is used, the assay kit includes at least (1) to (3) below.

(1) latex particles on which a first anti-AIM antibody is immobilized;

(2) latex particles on which a second anti-AIM antibody recognizing an epitope different from the first anti-AIM antibody is immobilized; and (3) an anti-IgM antibody.

In such an assay kit, the first anti-AIM antibody and the second anti-AIM antibody agglutinate via free AIM in the presence of anti-IgM antibody. The free AIM concentration in the biological sample can be obtained by detecting a degree of agglutination by using optical means.

The present invention will hereinafter specifically be described with examples; however, these examples do not limit the scope of the present invention. Unless otherwise described, % denotes % by weight.

EXAMPLES

Example 1: Measurement of Complex AIM and Free AIM Amount by Total AIM Measurement System 1. Separation of Human Specimen by Column Chromatography Size fractionation of 10 µL of a human specimen was performed by size exclusion chromatography (TSKgel G3000 SWXL, Tosoh) to obtain respective fractions of complex AIM and free AIM (complex AIM: fraction Nos. 6 and 7, free AIM: fraction Nos. 14 and 15). HPLC was performed by using a phosphate buffer at a flow rate of 1 mL/min to acquire 500 µL of each fraction.

2. Production of Anti-AIM Monoclonal Antibody-Bound Magnetic Beads

1) The absorbance of the anti-AIM monoclonal antibody dialyzed with 150 mM potassium phosphate buffer (pH 7.8) was measured and adjusted to Abs 0.5 by using the same buffer solution.

2) With the buffer solution, 1 mL (30 mg/mL) of Dynabeads M-450 Epoxy manufactured by Dynamic Biotech was washed 3 times, and 1 mL of the antibody solution of 1) was added. Rotary stirring was performed at 25° C. for 18 hours or more.

3) The beads prepared at 2) were washed twice with a bead blocking buffer [50 mM Tris, 150 mM NaCl, 0.1% BSA, 0.09% $NaN_3$, pH 7.8]. The anti-AIM monoclonal antibody remaining in the solution and not bound to the beads was removed by removing the buffer solution by washing. Subsequently, 1 mL of the bead blocking buffer was added and stirred, and rotary stirring was performed at 25° C. for 18 hours or more.

4) After washing the beads twice with the bead blocking buffer, 1 mL of the bead blocking buffer was added and stirred. These were used as anti-AIM monoclonal antibody-bound magnetic beads and stored at 4° C. until use.

3. Production of Ruthenium-Labeled Anti-AIM Monoclonal Antibody

1) To 312.5 µL of an anti-AIM monoclonal antibody solution (antibody having an epitope different from the anti-AIM monoclonal antibody bound to magnetic beads) dialyzed with 150 mM potassium phosphate buffer (pH 7.8), 14.1 µL of 10 mg/mL ruthenium complex (Origin Tag-NHS ESTER manufactured by IGEN) was added, and the solution was stirred for 30 minutes. Subsequently, 50 µL of 2M glycine was added, and the solution was stirred for 20 minutes.

2) A ruthenium complex-labeled anti-AIM monoclonal antibody was applied to gel filtration column chromatography (Sephadex G-25 manufactured by GE Healthcare Bioscience) packed in a glass tube with a diameter of 1 cm and a height of 30 cm to isolate and purify the non-labeling ruthenium complex and the ruthenium complex-labeled antibody. Elution was performed with 10 mM potassium phosphate buffer (pH 6.0).

4. Measurement of Fractions

1) From each of the complex AIM fractions (Nos. 6 and 7), 10 µL was taken to add a total of 20 µL to 200 µL of a reaction solution [50 mM HEPES, 50 mM NaCl, 0.05% Tween 20, 1 mM EDT-4Na, 0.5% BSA, 0.09% $NaCl_3$, 100 µg/mL Mouse IgG, pH 7.8] or an anti-IgM antibody-containing reaction solution. Similarly, 10 µL of each of the free AIM fractions (Nos. 14 and 15) was taken to add a total of 20 µL to 200 µL of the reaction solution or the anti-IgM antibody-containing reaction solution. For the anti-IgM antibody, a monoclonal antibody (HBR-6, HBR-20, adjusted to 50 µg/mL) or a polyclonal antibody (P0911 (Trina Bioreactives AG), adjusted to 0.125%) was used.

2) To the solution, 25 µL of antibody No. 12-bound magnetic beads diluted to a concentration of 0.5 mg/mL with a bead diluent [50 mM HEPES, 100 mM NaCl, 0.1% Tween 20, 1 mM EDT-4Na, 0.5% BSA, 0.09% $NaN_3$, pH 7.8] was added and reacted at 30° C. for 9 minutes (first reaction).

Subsequently, the magnetic beads were trapped with a magnet, the liquid in the reaction tube was extracted, and the magnetic beads were washed twice with 350 µL of washing liquid [50 mmol/L Tris HCl, 0.01% (W/V) Tween 20, 0.15 mol/L NaCl, pH 7.5] to remove non-specific binding substances other than the antigen-antibody reaction (BF separation).

3) Subsequently, 200 µL of a ruthenium-labeled antibody No. 12 diluted with a dilute solution for ruthenium [50 mM HEPES, 50 mM NaCl, 0.05% Tween 20, 1 mM EDT-4Na, 0.5% BSA, 0.09% $NaN_3$, 100 µg/mL mouse IgG, pH 7.8] to a concentration of 0.6 µg/mL was added and reacted at 30° C. for 9 minutes (second reaction).

The magnetic beads after the reaction were trapped with a magnet, the liquid in the reaction tube was extracted, and the magnetic beads were washed twice with 350 µL of the washing liquid to remove non-specific binding substances other than the antigen-antibody reaction (BF separation).

4) Subsequently, 300 µL of tripropylamine was placed in the reaction tube and mixed with the magnetic beads. By applying electrical energy in this state, the ruthenium complex emitted light, and the emission intensity was detected by a detector.

After the operation of adding the magnetic beads to the reaction tube, this was performed on an automatic ruthenium complex luminescence measuring machine, Picolumi III.

The results are shown in FIG. 1. When a count ratio of F6+F7 was lower than a standard, the non-specific reaction of the antibody to complex AIM was probably more suppressed. When a count ratio of F14+F15 was lower than a standard, the sensitivity of the antibody to free AIM was probably more reduced. In the measurement systems to which the anti-IgM antibody was added, the count ratio of F6+F7 was 37.4% (HBR-6), 55.8% (HBR-20), and 4.4% (P0911) with respect to the measurement system to which the anti-IgM antibody was not added, and the non-specific reaction of the anti-AIM antibody to the complex AIM was suppressed in all the measurement systems. Specifically, the nonspecific reaction was reduced by about 63% in the system to which HBR-6 was added as compared to the system in which HBR-6 was not added, the nonspecific reaction was reduced by about 44% in the system to which HBR-20 was added as compared to the system in which HBR-20 was not added, and the non-specific reaction was reduced by about 96% in the system to which P0911 was added as compared to the system in which P0911 was not added. Therefore, it was demonstrated that the non-specific reaction due to complex AIM can be suppressed by reacting the biological sample with the anti-AIM antibody in the presence of the anti-IgM antibody.

INDUSTRIAL APPLICABILITY

According to the present invention, the specificity of an anti-AIM antibody for free AIM can be improved in a biological sample containing complex AIM and free AIM.

The invention claimed is:

1. An immunoassay method for measuring an amount of free apoptosis inhibitor of macrophage (AIM) in a biological sample containing complex AIM and free AIM, the method comprising: bringing the biological sample into contact with an anti-AIM antibody in a presence of an added anti-IgM antibody at a concentration sufficient to reduce a non-specific reaction.

2. The immunoassay method according to claim 1, wherein the biological sample is a body fluid sample.

3. The immunoassay method according to claim 1, wherein the biological sample is blood, serum, plasma, or urine.

4. The immunoassay method according to claim 1, wherein the anti-AIM antibody is a polyclonal antibody.

5. A method for reducing a non-specific reaction in an immunoassay for measuring an amount of free apoptosis inhibitor of macrophage (AIM) in a biological sample containing complex AIM and free AIM, the method comprising: bringing the biological sample into contact with an anti-AIM antibody in a presence of an added anti-IgM antibody at a concentration sufficient to reduce said non-specific reaction.

6. The method according to claim 5, wherein the biological sample is a body fluid sample.

7. The method according to claim 5, wherein the non-specific reaction is due to IgM in the biological sample.

* * * * *

SEQUENCE LISTING

<160> NUMBER OF SEQ ID NOS: 4

<210> SEQ ID NO 1
<211> LENGTH: 347
<212> TYPE: PRT
<213> ORGANISM: human

<400> SEQUENCE: 1

```
Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
            20                  25                  30

Cys Glu Gly Arg Val Glu Val Glu Gln Lys Gly Gln Trp Gly Thr Val
        35                  40                  45

Cys Asp Asp Gly Trp Asp Ile Lys Asp Val Ala Val Leu Cys Arg Glu
    50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
        275                 280                 285

Lys Ser Leu Ser Pro Ser Phe Arg Asp Arg Lys Cys Tyr Gly Pro Gly
    290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Gly
            340                 345
```

<210> SEQ ID NO 2
<211> LENGTH: 102

```
<212> TYPE: PRT
<213> ORGANISM: human

<400> SEQUENCE: 2

Val Arg Leu Val Gly Gly Leu His Arg Cys Glu Gly Arg Val Glu Val
1               5                   10                  15

Glu Gln Lys Gly Gln Trp Gly Thr Val Cys Asp Asp Gly Trp Asp Ile
            20                  25                  30

Lys Asp Val Ala Val Leu Cys Arg Glu Leu Gly Cys Gly Ala Ala Ser
        35                  40                  45

Gly Thr Pro Ser Gly Ile Leu Tyr Glu Pro Pro Ala Glu Lys Glu Gln
    50                  55                  60

Lys Val Leu Ile Gln Ser Val Ser Cys Thr Gly Thr Glu Asp Thr Leu
65                  70                  75                  80

Ala Gln Cys Glu Gln Glu Glu Val Tyr Asp Cys Ser His Asp Glu Asp
                85                  90                  95

Ala Gly Ala Ser Cys Glu
            100

<210> SEQ ID NO 3
<211> LENGTH: 102
<212> TYPE: PRT
<213> ORGANISM: human

<400> SEQUENCE: 3

Val Arg Leu Ala Asp Gly Pro His Cys Lys Gly Arg Val Glu Val
1               5                   10                  15

Lys His Gln Asn Gln Trp Tyr Thr Val Cys Gln Thr Gly Trp Ser Leu
            20                  25                  30

Arg Ala Ala Lys Val Val Cys Arg Gln Leu Gly Cys Gly Arg Ala Val
        35                  40                  45

Leu Thr Gln Lys Arg Cys Asn Lys His Ala Tyr Gly Arg Lys Pro Ile
    50                  55                  60

Trp Leu Ser Gln Met Ser Cys Ser Gly Arg Glu Ala Thr Leu Gln Asp
65                  70                  75                  80

Cys Pro Ser Gly Pro Trp Gly Lys Asn Thr Cys Asn His Asp Glu Asp
                85                  90                  95

Thr Trp Val Glu Cys Glu
            100

<210> SEQ ID NO 4
<211> LENGTH: 103
<212> TYPE: PRT
<213> ORGANISM: human

<400> SEQUENCE: 4

Leu Arg Leu Val Gly Gly Asp Asn Leu Cys Ser Gly Arg Leu Glu Val
1               5                   10                  15

Leu His Lys Gly Val Trp Gly Ser Val Cys Asp Asp Asn Trp Gly Glu
            20                  25                  30

Lys Glu Asp Gln Val Val Cys Lys Gln Leu Gly Cys Gly Lys Ser Leu
        35                  40                  45

Ser Pro Ser Phe Arg Asp Arg Lys Cys Tyr Gly Pro Gly Val Gly Arg
    50                  55                  60
```

-continued

```
Ile Trp Leu Asp Asn Val Arg Cys Ser Gly Glu Glu Gln Ser Leu Glu
65                  70                  75                  80

Gln Cys Gln His Arg Phe Trp Gly Phe His Asp Cys Thr His Gln Glu
                85                  90                  95

Asp Val Ala Val Ile Cys Ser
            100
```